US00PP34861P2

(12) United States Plant Patent
Brown

(10) Patent No.: US PP34,861 P2
(45) Date of Patent: Dec. 20, 2022

(54) ***ALOE* PLANT NAMED 'MOBAL 33'**

(50) Latin Name: *Aloe humilis*
Varietal Denomination: MOBAL 33

(71) Applicant: Morgan Oates & Brown Pty Ltd, Macquarie Fields (AU)

(72) Inventor: Graham Brown, Bowral (AU)

(73) Assignee: Morgan Oates & Brown Pty Ltd, Macquarie Fields (AU)

( * ) Notice: Subject to any disclaimer, the term of this patent is extended or adjusted under 35 U.S.C. 154(b) by 0 days.

(21) Appl. No.: 17/803,441

(22) Filed: Jul. 11, 2022

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373, 263.1, 443
CPC ... A01H 5/12; A01H 5/00; A01H 6/32; A01H 6/00
See application file for complete search history.

*Primary Examiner* — June Hwu
(74) *Attorney, Agent, or Firm* — Samuel R. McCoy, Jr.

(57) ABSTRACT

A new and distinct *Aloe humilis* plant named 'MOBAL 33' which is characterized by a globular profile with linear succulent foliage arranged in a basal rosette that eventually forms a short stem with age, linear foliage with an upward and outward attitude with the distal portion of the lamina strongly curled under, dark green foliage that is thinly covered with greyed-green epicuticular wax, and prominent spinose leaf margins with large spines which generally appear to be tipped near-white. The new variety has shown to be uniform and stable in the resulting generations from asexual propagation.

3 Drawing Sheets

Latin name of the genus and species: The Latin name of the genus and species of the novel variety disclosed herein is *Aloe humilis*.

Variety denomination: The inventive variety of *Aloe* disclosed herein has been given the variety denomination 'MOBAL 33'.

BACKGROUND OF THE INVENTION

Parentage: 'MOBAL 33' is a seedling selection resulting from the open pollination of a cultivated population of unnamed *Aloe humilis* plants (unpatented). The exact parentage is unknown. The crossing was made by the inventor in May of 2011 at a commercial ornamental plant nursery in Macquarie Fields, New South Wales, Australia. Seeds were harvested from a plurality of plants within in the population and were subsequently grown to a mature size at a secure greenhouse in Picton, New South Wales, Australia. One seedling resulting from said cross was observed to exhibit unique growth and foliage characteristics and was isolated for further evaluation in order to confirm the distinctness and stability of the characteristics first observed. Upon confirmation of distinctness and stability, the new plant was selected in June of 2012 for commercialization and given the name, 'MOBAL 33'.

Asexual Reproduction: The variety now called 'MOBAL 33' was first asexually propagated by meristematic tissue culture in December of 2012 at a laboratory in Picton, New South Wales, Australia. 'MOBAL 33' has since been vegetatively propagated through ten additional generations. Through subsequent generations, the unique features of this cultivar are stable and reproduced true to type.

SUMMARY OF THE INVENTION

The cultivar 'MOBAL 33' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'MOBAL 33'. These characteristics in combination distinguish 'MOBAL 33' as a new and distinct *Aloe humilis* cultivar:

1. 'MOBAL 33' exhibits a globular profile with linear succulent foliage arranged in a basal rosette, eventually forms a short stem with age; and
2. 'MOBAL 33' exhibits linear foliage with an upward and outward attitude with the distal portion of the lamina strongly curled under; and
3. 'MOBAL 33' exhibits dark green foliage that is thinly covered with greyed-green epicuticular wax; and
4. 'MOBAL 33' exhibits prominent spinose leaf margins with large spines which generally appear to be tipped near-white.

BOTANICAL DESCRIPTION OF THE PLANT

Figure 1:
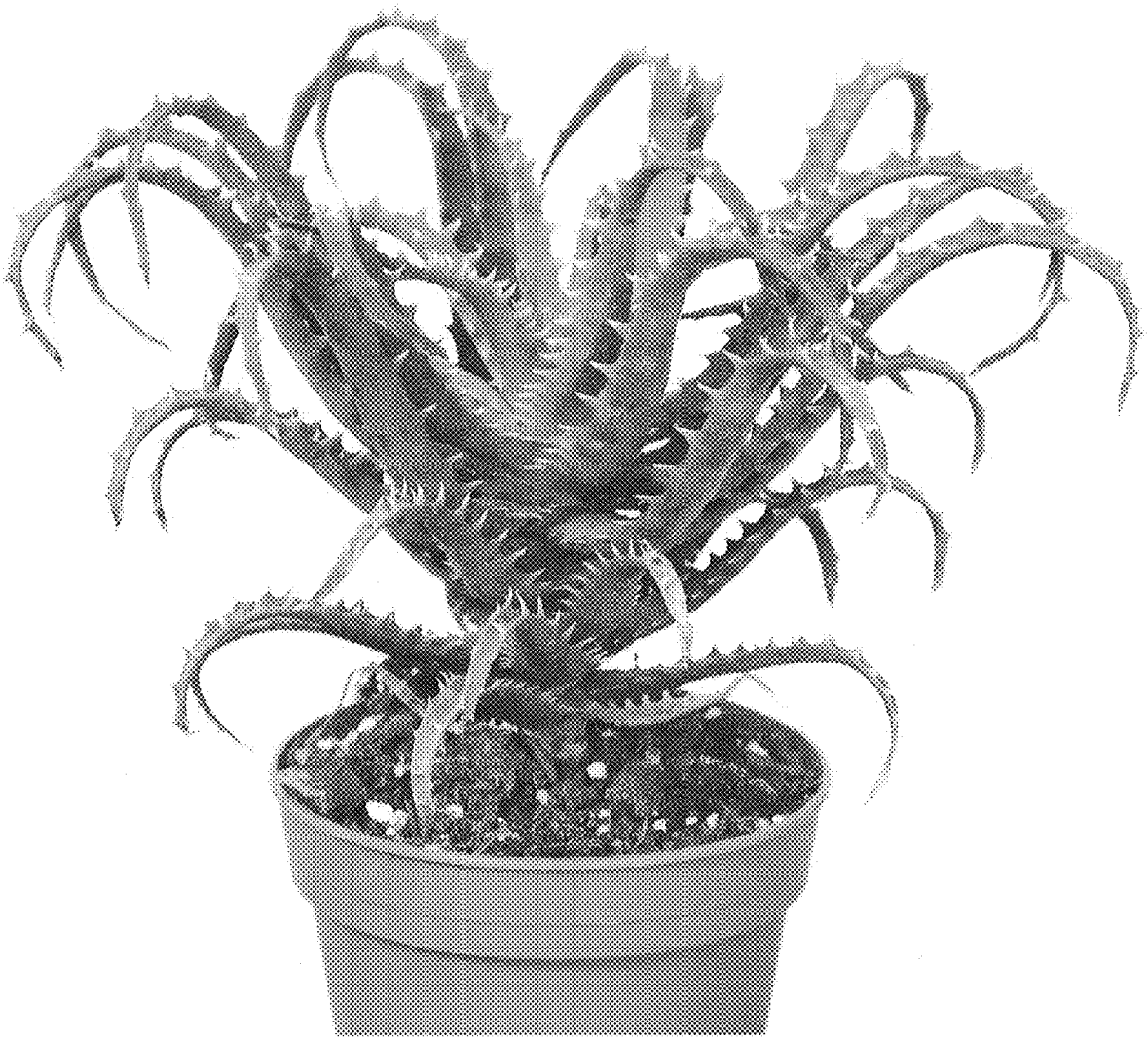
FIG. 1 illustrates, as nearly true as it is reasonably possible to make the same in color photographs of this type, an exemplary plant of 'MOBAL 33' grown in a commercial greenhouse in Picton, New South Wales, Australia. This plant is approximately 1-year-old, shown planted in a 13 cm container.
Figure 2:
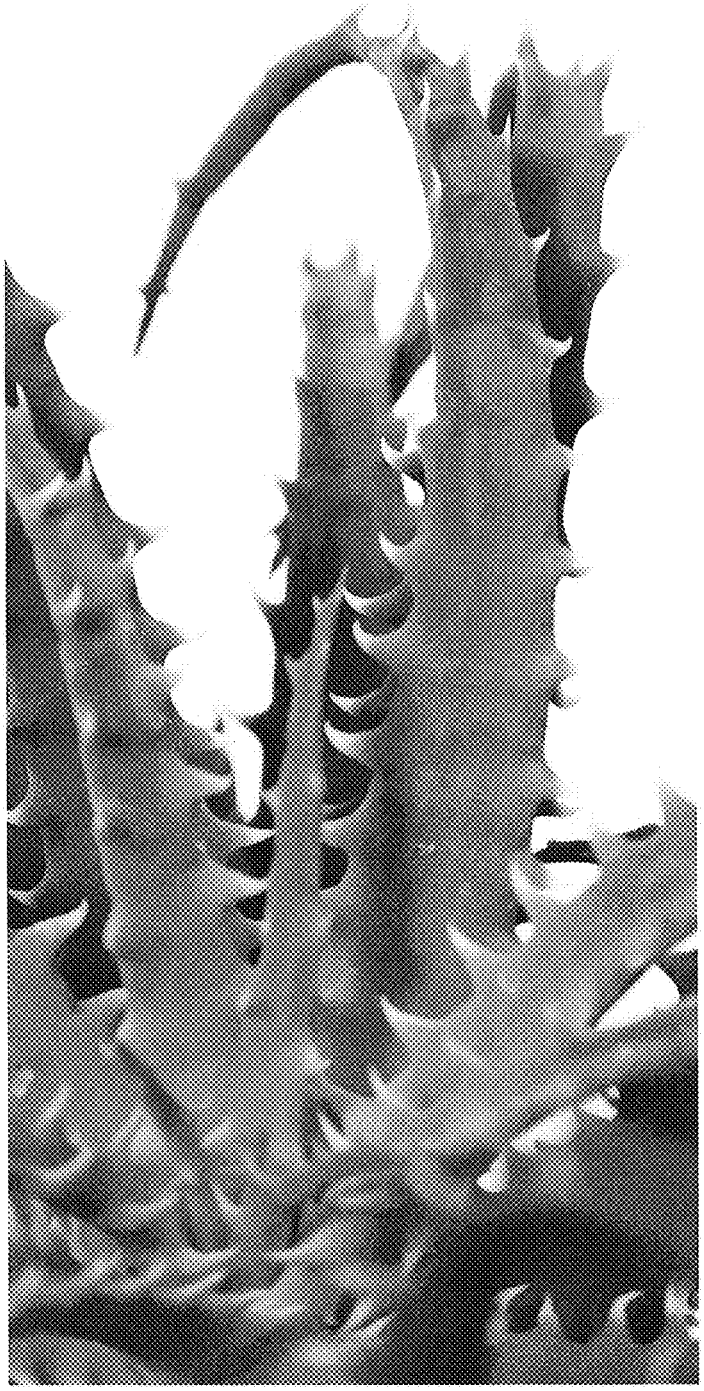
FIG. 2 illustrates, as nearly true as it is reasonably possible to make the same in color photographs of this type, the adaxial surface of the mature foliage 'MOBAL 33'.
Figure 3:
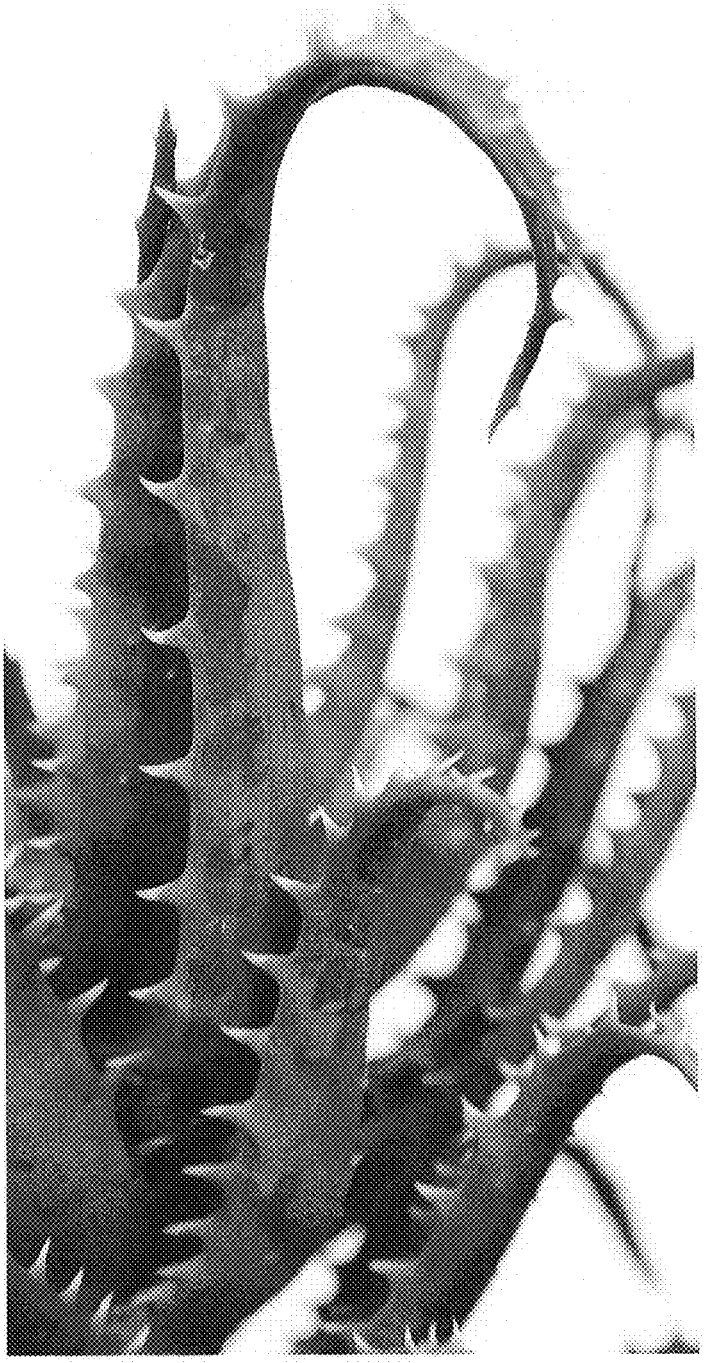
FIG. 3 illustrates, as nearly true as it is reasonably possible to make the same in color photographs, of this type, the abaxial surface of the mature foliage 'MOBAL 33'.

The following observations and measurements made in June of 2021 describe averages from a sample set of six specimens of 1-year-old 'MOBAL 33' plants grown in 13 cm nursery containers at commercial greenhouse in Picton, New South Wales, Australia. Plants were produced using conventional greenhouse production protocols for *Aloe* which consisted of minimal subsurface irrigation, fertilizer applications, and chemical pest control measures against thrips as required. No other chemical pest and disease control measures were taken. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with. younger plants. 'MOBAL 33' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'MOBAL 33' and a comparison with the seed parent and closest known comparator are provided below.

Plant description:

*Growth habit*.—Succulent perennial with foliage growing in an upright, non-branched basal rosette, eventually forming a short stem.

*Plant form*.—Globular.

*Height from soil level to top of foliar plane*.—17.7 cm.

*Plant spread*.—Average of 26.2 cm.

*Growth rate*.—Moderate rate of growth.

*Plant vigor*.—Moderately to highly vigorous. Type — Meristematic tissue culture micropropagation. Time to initiate rooting — Approximately 6 weeks at an approximate temperature of 21 degrees Celsius. Crop time — Approximately 12 weeks to produce a marketable plant in a 12 cm container.

*Disease and pest resistance or susceptibility*.—Neither resistance nor susceptibility to typical *Aloe humilis* pests and diseases has been observed.

*Environmental tolerances*.—Adapt to, at least, USDA Zones 10 to 12 and temperatures as high as 40 .degrees Celsius; moderate tolerance to rain yet drought tolerant once established; high tolerance to wind.

Root system:

*General*.—Fine, well-branched fibrous roots.

Stems:

*Branching habit*.—Leaves in a basal rosette, eventually forming a short, unbranched stem with age; no lateral branching.

*Quantity of main stems*.—1.

*Quantity of lateral branches*.—None.

*Main stem dimensions*.—9.9 cm long and 1.4 cm in diameter.

*Internode length*.—0.2 cm.

*Cross section*.—Rounded, formed by leaf sheaths.

*Attitude*.—Nearly vertical.

*Strength*.—Moderately strong.

*Texture and luster*.—Glabrous and slightly glossy.

*Color, when developing*.—Yellow-green, nearest to RHS 147D yet lighter.

*Color of mature stem*.—Yellow-green, nearest to RHS 145D.

*Color at internodes*.—Yellow-green, nearest to RHS 145D.

*Color at the base*.—Greyed-brown, nearest to RHS 199D; veined darker, nearest to RHS 199A.

Foliage:

*Arrangement*.—Spirally arranged in a basal rosette.

*Division*.—Simple.

*Attachment*.—Sessile.

*Quantity*.—Approximately 45 leaves per rosette.

*Shape*.—Linear.

*Dimensions*.—17.9 cm long, 2.6 cm wide, including the marginal teeth, and 0.8 cm thick.

*Aspect*.—Flattened terete; moderately concave.

*Attitude*.—Upright and outward, at an average angle of 70 degrees from horizontal, with the distal portion of the lamina and apex strongly curling downward.

*Apex*.—Long-apiculate.

*Base*.—Broad cuneate; decurrent. Sheath length — 0.4 cm. Sheath width — 2.4 cm. Sheath color — Both inner and outer surfaces are yellow-green, nearest to a mixture of RHS 145C and 145D.

*Margin*.—Prominently spinose. Quantity of spines — 33 per leaf, on average. Attitude of spines — Outward to upward. Dimensions of spines — 0.5 cm long and 0.25 cm wide at the base. Color of the juvenile spines — Both the adaxial and abaxial surfaces are green, nearest to RHS 143B, and transition to a mixture of yellow-green and green-white, distally, nearest to RHS 145D and 157A. Color of the mature spines — Both the adaxial and abaxial surfaces are yellow-green, nearest to RHS 144B, and transition to a lighter shade of yellow-green, distally, nearest to RHS 144D.

*Pubescence and texture of the adaxial surface*.—Glabrous, smooth, and lightly covered with a thin layer of epicuticular wax.

*Pubescence and texture of the abaxial surface*.—Glabrous, smooth, and lightly covered with a thin layer of epicuticular wax.

*Luster of the adaxial surface*.—Matte.

*Luster of the abaxial surface*.—Matte.

*Color*.—Juvenile foliage, adaxial surface — Green, nearest to RHS 143A, and fading to yellow-green towards the base, nearest to RHS 144B; tipped lighter, nearest to RHS 144D. The epicuticular wax is colored greyed-green, nearest to RHS 189A. Juvenile foliage, abaxial surface — Green, nearest to RHS 138A, and fading to yellow-green towards the base, nearest to RHS 145A; tipped lighter, nearest to RHS 144D. The epicuticular wax is colored greyed-green, nearest to RHS 189A. Mature foliage, adaxial surface — Green, nearest to RHS NN137A. The epicuticular wax is colored greyed-green, nearest to RHS 189A. Mature foliage, abaxial surface — Green, nearest to RHS NN137B The epicuticular wax is colored greyed-green, nearest to RHS 189A.

*Venation*.—No visible venation.

*Petiole*.—No petiole; leaves are sessile.

Inflorescence: No flowering has been observed to date.

COMPARISONS WITH THE PARENT PLANTS

The exact parentage of the new cultivar 'MOBAL 33' is unknown. However, several characteristics distinguish the claimed plant from plants that typify the species, *Aloe humilis* (not patented). Those differences are described in Table 1 below.

TABLE 1

| Characteristic | 'MOBAL 33' | *Aloe humilis* |
|---|---|---|
| Growth rate. | Faster growing than *Aloe humilis*. | Slower growing than 'MOBAL 33'. |
| Plant size. | Larger than *Aloe humilis*. | Smaller than 'MOBAL 33'. |
| Foliage attitude. | Upright and outward, becoming strongly curled downward along the distal portion of the lamina. | Generally upright and slightly curled upward or inward. |
| Presence of spines on the laminar surfaces. | Devoid of spines. | Spines present. |

COMPARISON WITH THE CLOSEST KNOWN COMPARATOR

Plants of the new cultivar 'MOBAL 33' differ from the most similar variety known to the inventor, *Aloe humilis* 'Hedgehog' (unpatented), in the following characteristics described in Table 2 below.

TABLE 2

| Characteristic | 'MOBAL 33' | 'Hedgehog' |
|---|---|---|
| Growth rate. | Faster growing than 'Hedgehog'. | Slower growing than 'MOBAL 33'. |
| Plant size. | Larger than 'Hedgehog'. | Smaller than 'MOBAL 33'. |
| Foliage attitude. | Upright and outward, becoming strongly curled downward along the distal portion of the lamina. | Generally upright and slightly curled downward near the apex. |

That which is claimed is:

1. A new and distinct variety of *Aloe humilis* plant named 'MOBAL 33', substantially as described and illustrated herein.

* * * * *